United States Patent [19]
Greive

[11] Patent Number: 6,059,484
[45] Date of Patent: May 9, 2000

[54] GUIDE WIRE INTRODUCER ASSEMBLY WITH GUIDE WIRE GRIP AND RELEASE MEANS

[76] Inventor: Michael Greive, Kirchstr. 4, D-48308 Senden-Ottmarsbocholt, Germany

[21] Appl. No.: 09/077,043
[22] PCT Filed: Nov. 14, 1996
[86] PCT No.: PCT/EP96/04980
  § 371 Date: Aug. 19, 1998
  § 102(e) Date: Aug. 19, 1998
[87] PCT Pub. No.: WO97/18850
  PCT Pub. Date: May 29, 1997

[30] Foreign Application Priority Data

Nov. 17, 1995 [DE] Germany ............................ 195 42 912

[51] Int. Cl.[7] .................................................. A61M 5/00
[52] U.S. Cl. ........................... 403/305; 604/264; 600/585; 128/912
[58] Field of Search ..................... 604/264, 523, 604/528, 159; 128/912; 600/434, 585; 403/305

[56] References Cited

U.S. PATENT DOCUMENTS

| | | | |
|---|---|---|---|
| 4,214,779 | 7/1980 | Losell | 285/93 |
| 4,552,554 | 11/1985 | Gould et al. | 604/51 |
| 4,844,092 | 7/1989 | Rydell et al. | 128/772 |
| 4,860,757 | 8/1989 | Lynch et al. | 128/657 |
| 4,973,329 | 11/1990 | Park et al. | 606/1 |
| 5,147,334 | 9/1992 | Moss | 604/264 |
| 5,163,921 | 11/1992 | Feiring | 604/247 |
| 5,273,042 | 12/1993 | Lynch et al. | 128/657 |
| 5,279,573 | 1/1994 | Klosterman | 604/171 |
| 5,279,588 | 1/1994 | Nicoletti et al. | 604/250 |
| 5,282,479 | 2/1994 | Havran | 128/772 |
| 5,366,444 | 11/1994 | Martin | 604/159 |
| 5,389,087 | 2/1995 | Miraki | 604/247 |
| 5,390,669 | 2/1995 | Stuart et al. | 604/264 X |
| 5,392,778 | 2/1995 | Horzewski | 128/657 |
| 5,438,993 | 8/1995 | Lynch et al. | 128/657 |
| 5,448,993 | 9/1995 | Lynch et al. | 128/657 |

FOREIGN PATENT DOCUMENTS

| | | |
|---|---|---|
| 0 371 486 | of 1990 | European Pat. Off. . |
| 0 554 754 A1 | of 1993 | European Pat. Off. ....... A61M 25/01 |
| 2701212 | 8/1994 | France ................................ 604/264 |
| 2701213 | 8/1994 | France ................................ 604/264 |
| 28 05 416 A1 | of 0000 | Germany . |
| 93 19 838 | of 1994 | Germany ..................... A61M 25/01 |
| 2 215 703 | of 1989 | United Kingdom . |

*Primary Examiner*—Lynne H. Browne
*Assistant Examiner*—David E. Bochna
*Attorney, Agent, or Firm*—Baker & Daniels

[57] ABSTRACT

An apparatus to stretch one end of a catheter guide wire, and to secure the catheter guide wire in a dispenser tube is provided, including an introduction aid and a connection element. The introduction aid includes an elongate hollow element having an open distal end and an open proximal end, a cylindrical section having an undercut and a conical section tapering away from the cylindrical section. The cylindrical section contains a longitudinal U-shaped slit defining a flexible tongue, where the flexible tongue is adapted for pressing into the cylindrical section. The connection element includes a proximal connector, a tubular distal connector, and a central section between the proximal and distal connectors. The central section is open such that the guide wire is accessible, and includes an advancing surface. The proximal connector connects to the end of a catheter guide wire dispenser tube. The distal connector is adapted to be inserted into the cylindrical section such that the elongate hollow element and the connection element may move longitudinally relative to one another between first and second positions. A retaining device disposed on the distal connector grips the undercut around the cylindrical section in the second position. The flexible tongue is pressed into the distal connector to engage the catheter guide wire in the first position, and is released from the catheter guide wire in the second position.

10 Claims, 6 Drawing Sheets

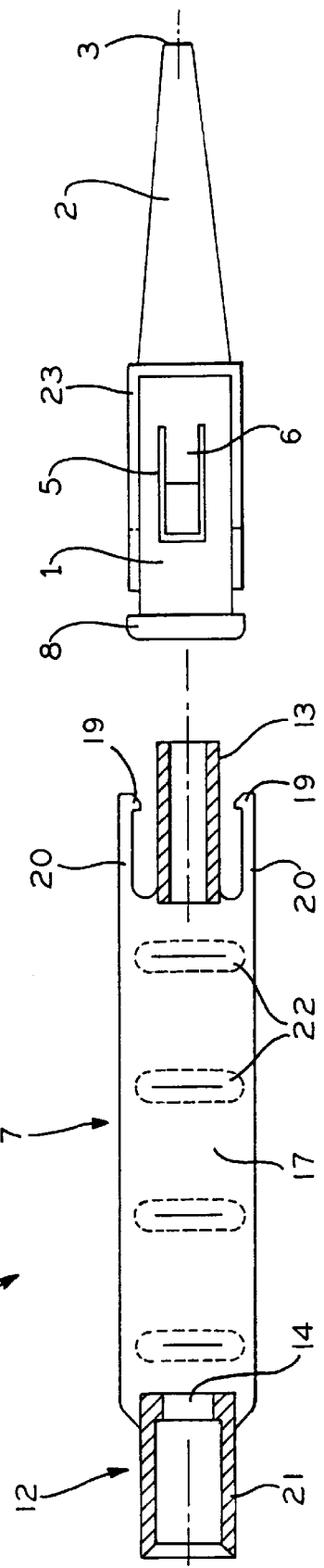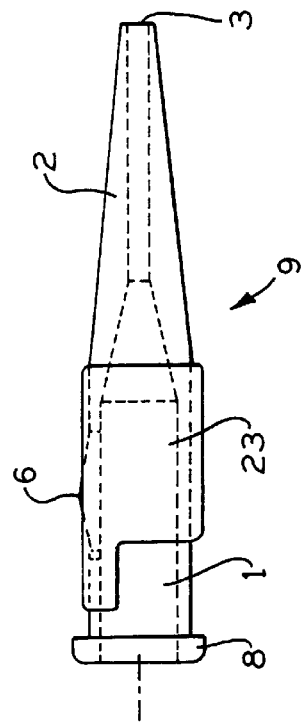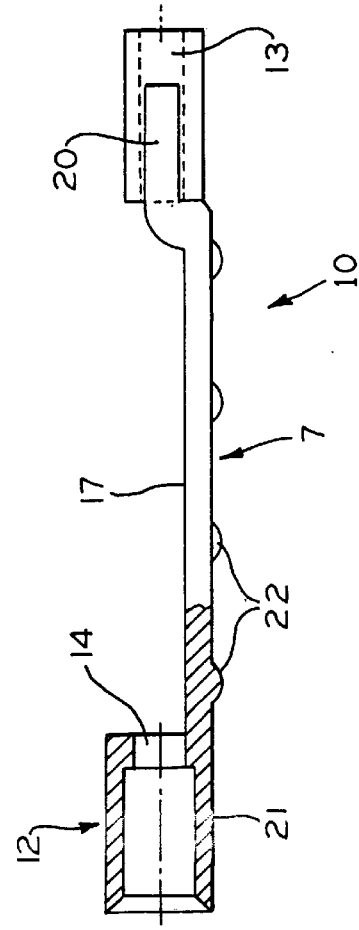

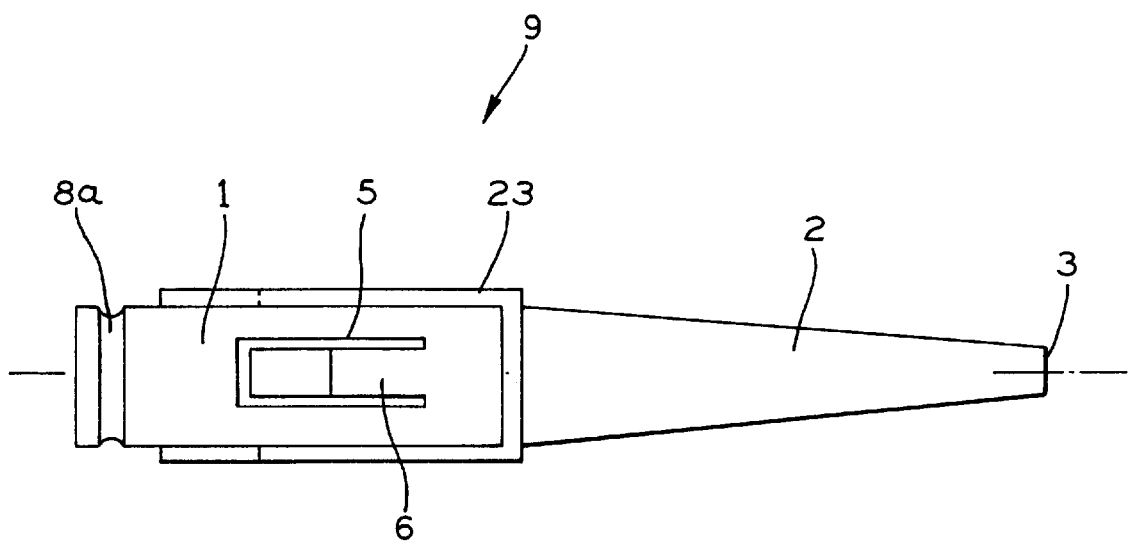
FIG_2A

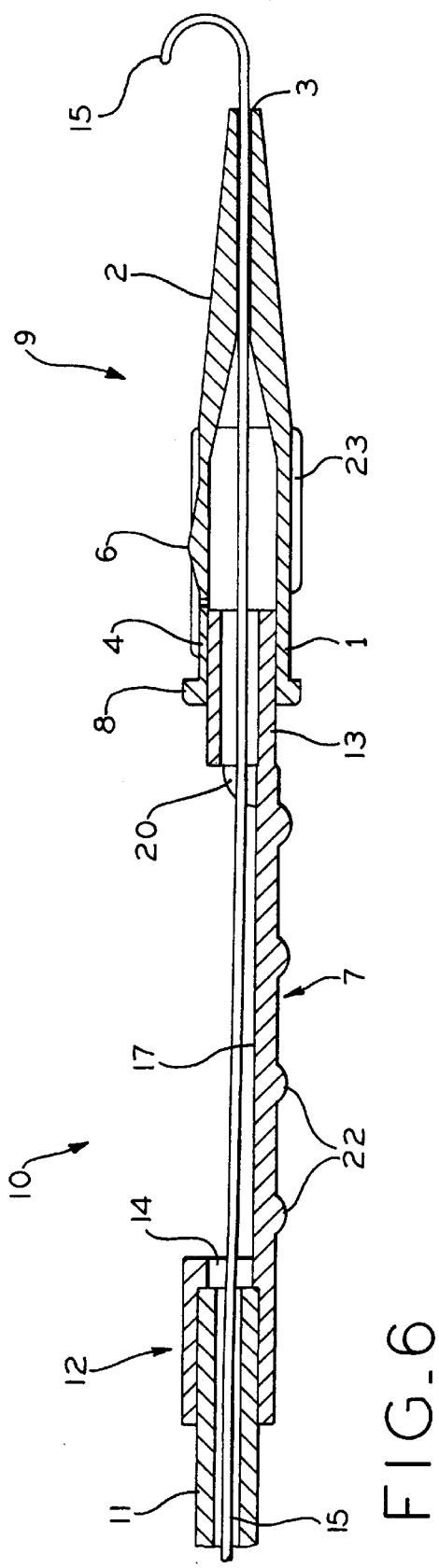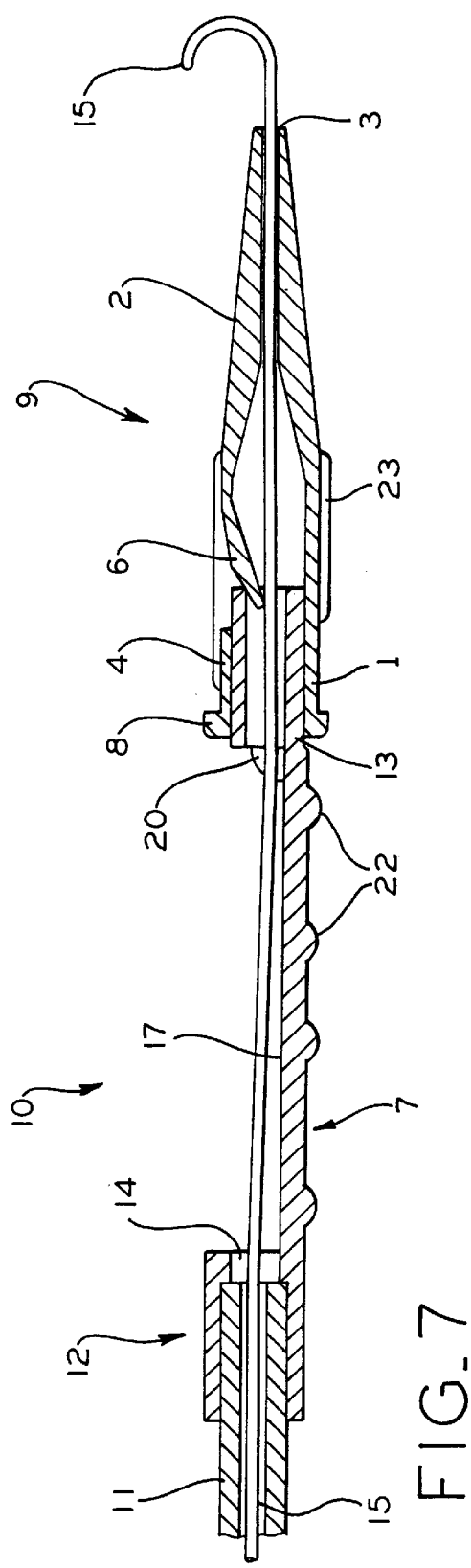

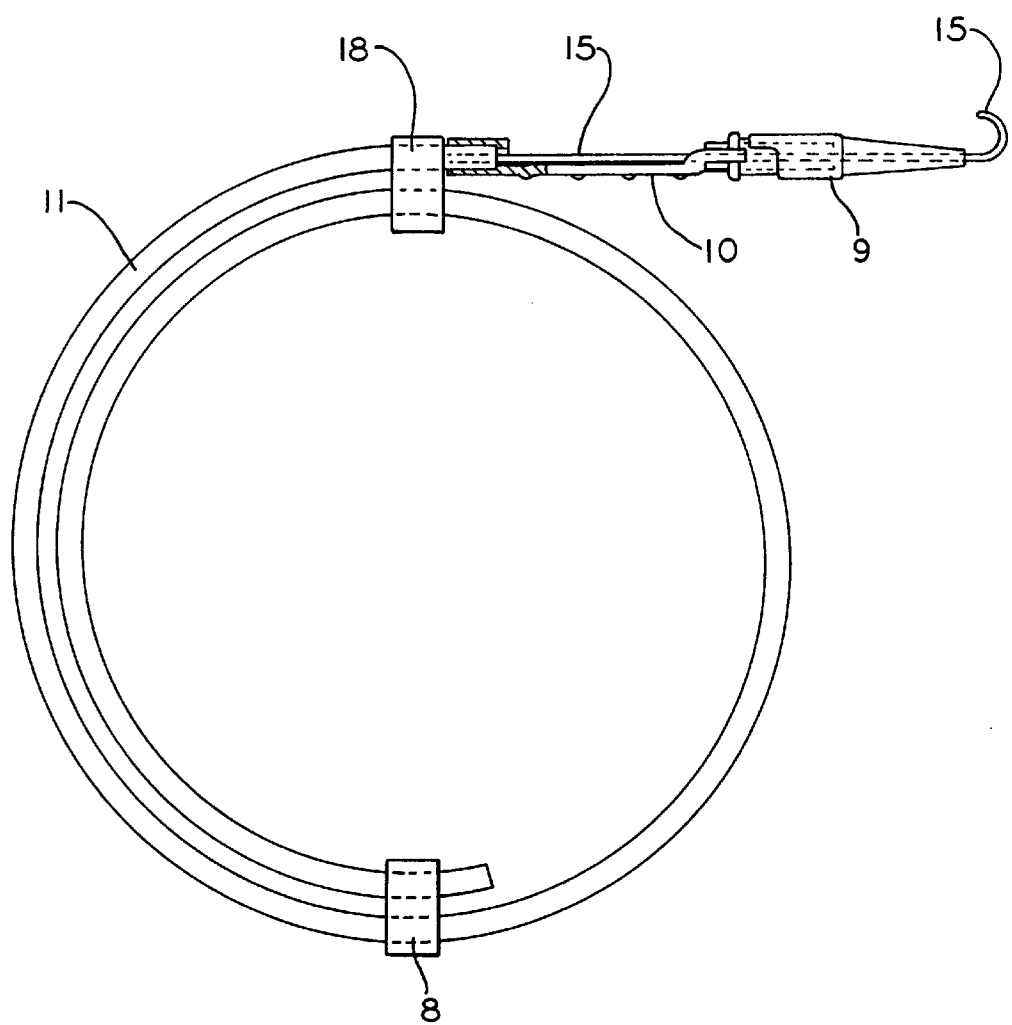
FIG_8

GUIDE WIRE INTRODUCER ASSEMBLY WITH GUIDE WIRE GRIP AND RELEASE MEANS

BACKGROUND OF THE INVENTION

1. Field of the Invention

The present invention relates to an introduction aid for stretching a guide wire, in particular a Seldinger wire with a flexible tip which is curved in a J shape, and securing the guide wire in a dispenser tube and to a connection element for connecting the introduction aid to the dispenser tube.

2. Description of Related Art

Used for introducing a single-lumen or multi-lumen catheter into a blood vessel is a guide wire which is brought through a puncture point to the target site and over which subsequently the catheter is advanced. This is called the Seldinger technique, which is performed using a Seldinger wire which is distinguished by a highly flexible tip which is curved in a J shape. Since guide wires may have a considerable length (0.4 to >1 m) and, apart from the highly flexible tip, have a certain elastic stiffness, the user is impeded by the end of the guide wire which projects freely out of the patient's body, and it is important to keep this end in the form of a loop. For this purpose, and for the purpose of transport, the guide wire is accommodated in a rigid dispenser tube which is converted into a coil and kept in this shape, and from which it can be released into the patient's body through an introduction kit. The dispenser tube which is converted into a coil is normally kept in place with the aid of separate clips which have longitudinal slits and are designed as double or triple clasps and in each case clamp together adjacent tube strands. The dispenser tube consists of a solid plastic, for example polypropylene, and its internal diameter is larger than the external diameter of the guide wire so that the latter slides very smoothly in the lumen of the tube. In this case, the J-shaped tip of the guide wire is stretched using an introduction aid at the junction between the end of the dispenser tube and the inlet of the catheter kit, for example a needle attachment. The introducer is provided with a pipe whose internal diameter is only slightly larger than the diameter of the guide wire so that the J-shaped tip is stretched straight. In the packaged state, the J-shaped tip of the guide wire projects beyond the front opening of the channel of the pipe so that the curvature retains its original radius and is not fatigued during the storage time due to permanent stretching in the pipe. One problem which arises is that the guide wire which slides smoothly in the dispenser tube may slip out of the dispenser during transport, which results in kinking in the packaging.

German utility model 93 19 838.8 describes an introduction aid for catheter guide wires which solves this problem. It discloses a device for securing and stretching the ends of guide wires, which comprises an elongate hollow element open at both ends, with a cylindrical section and a conical section which tapers towards the end, with a U-shaped slit extending in the longitudinal direction being present in the wall of the hollow element, so that a tongue which can be pressed into the inside of the hollow element is formed between the legs of the U-shaped slit open towards the end. A clamping fit of this device on the dispenser tube is achieved by the device being pushed onto the tube until the tongue is situated in the inside of the tube and, by means of the spring action, fixes the end of the tube in the cylindrical section of the device. The tongue, which in this way is pressed further inwards, secures the catheter guide wire against displacement in the longitudinal direction. In order to be able to introduce the J-shaped tip of the guide wire into a needle, the user must hold the dispenser tube with one hand and use the other hand to grip the introduction aid and pull it out of the end of the tube. The user must then use the hand holding the dispenser tube additionally to grip the guide wire and, with the other hand, pull the introduction aid over the J tip so that the J-shaped end is stretched in the introducer. After this, the user introduces the introduction aid with completely retracted guide wire into the attachment of the needle which has already been used for puncture. While he holds the introducer and end of the needle with one hand, he is able to advance the guide wire into the vein with the other hand. This manipulation is relatively involved because the user always requires both hands.

The dispenser disclosed in U.S. Pat. No. 5,125,906 did not have this disadvantage and is distinguished by being amendable to operation with one hand. This is attributable to the fact that an axial section of the introduction aid between a sleeve-like connection part with a closed wall for the dispenser tube and the pipe for stretching the J-shaped tip is bridged by an advancing surface and is open to the outside so that a finger or the thumb of the hand holding the introduction aid can be used to displace the guide wire crossing the axial section. A handle is located on the underside of the axial section bridged by the advancing surface, in order to facilitate operation by the user with one hand, and the end of the handle has a clamp for fastening the proximal end of the dispenser tube. The pipe channel and the guide wire passage are arranged coaxially, resulting in the guide wire being displaceable smoothly and without inhibition, which may lead to the guide wire slipping out in an unwanted manner during transport.

A dispenser which has an introduction aid and which can be operated with one hand and, at the same time, secures the guide wire against unwanted slipping out is described in European published specification 587 984. The introduction aid disclosed therein differs from that in U.S. Pat. No. 5,125,906 in that the longitudinal axes of the guide wire passage of the connection part and of the channel of the pipe, which is provided at an axial distance therefrom, for stretching the J-shaped tip run in planes which are offset with respect to one another, resulting in a self-inhibiting effect for the guide wire which is accommodated in the dispenser tube which is converted into a loop, which is intended to prevent the wire slipping out or to one side during storage and transport. However, it has emerged in practice that the offsetting is insufficient in fact to stop the wire slipping out. Just like the introduction aid from U.S. Pat. No. 5,125,906, the introduction aid described in European published specification 587 984 also not only grips at the distal end of the dispenser tube but likewise has a clamp or a clip which is fastened at the proximal end of the dispenser tube or, in the case of longer tubes, on the middle region thereof.

U.S. Pat. No. 5,282,479 relates to another introduction aid which can be operated with one hand and has transport securing. The introduction aid has at its proximal end at least two flexible lugs whose total extent in the unbraced state is greater than the internal diameter of the dispenser tube and which are forced into the dispenser tube. The guide wire is thus clamped firmly between the lugs in order to prevent the wire slipping out during transport. The dispenser tube has at its distal end a number of openings which corresponds to the number of flexible lugs, into which openings the lugs engage on use of the introduction aid after rotation thereof, and relax and release the guide wire so that the latter can be pushed out of the dispenser. Another opening in the form of an elongate slit is located in the dispenser tube itself and permits the user not only to release the transport securing with one hand but also to advance the wire out of the dispenser. The disadvantage in this case is that, during fabrication, the dispenser tube must itself be altered, which is associated with additional industrial complexity.

SUMMARY OF THE INVENTION

The present invention is therefore based on the problem of providing an introduction aid which is distinguished by being amenable to operation with one hand and, at the same time, exerts the function of a transport securing and, moreover, avoids the disadvantages of the introduction aids disclosed hitherto.

This problem is solved by an introduction aid for stretching one end of a guide wire and securing the guide wire in a dispenser tube, which aid has an elongate hollow element open at both ends, with an essentially cylindrical section and a conical section which tapers towards the distal end, a U-shaped slit extending in the longitudinal direction being present in the wall of the hollow element so that a tongue which can be pressed into the inside of the hollow element is formed between the legs of the U-shaped slit open towards the distal end, characterized in that the cylindrical section has at the proximal end an undercut, and a connection element for connecting the introduction aid to the dispenser tube, which element has a proximal connector for fastening the distal end of the dispenser tube, a tubular distal connector onto which the introduction aid can be pushed with its cylindrical section, and remains displaceable in the longitudinal direction after connection has taken place, and a central piece located between them and having an advancing surface, which is freely accessible from outside, for the guide wire, a retaining means being present on the distal connector and/or at the distal end of the central piece and gripping the undercut of the introduction aid at maximum excursion in the distal direction of the introduction aid which has been fitted onto the distal connector in order to limit the movement of the aid in the longitudinal direction.

The invention also relates to a kit comprising this introduction aid and this connection element.

It is self-evident that the functions of "undercut" on the one hand and "retaining means" on the other hand can also be exchanged with one another, that is to say the connection element has an undercut while the introduction aid possesses a retaining means. The present invention is therefore also directed at a connection element for connecting an introduction aid which is used to stretch one end of a guide wire and secure a guide wire in a dispenser tube to the dispenser tube, which element has a proximal connector for fastening the distal end of the dispenser tube, an essentially tubular distal connector onto which the introduction aid can be pushed, and a central piece located between them and having an advancing surface which is freely accessible from outside, with an outer tube, or an outer tube which is perforated one or more times along the extent of the tube, being arranged around the tubular distal connector and partly encircling the introduction aid which has been pushed on and having at its distal end an undercut, and an introduction aid for stretching one end of a guide wire and securing the guide wire in a dispenser tube, which aid can be connected by such a connection element to the dispenser tube and has an elongate hollow element open at both ends, with an essentially cylindrical section which can be pushed onto the distal connector of the connection element and, after connection has taken place, remains displaceable in the longitudinal direction, and a conical section which tapers towards the distal end, there being present in the wall of the hollow element a U-shaped slit extending in the longitudinal direction, so that a tongue which can be pressed into the inside of the hollow element is formed between the legs of the U-shaped slit open towards the distal end, characterized in that a retaining means is present on the cylindrical section and grips the undercut of the outer tube on the distal connection part of the connection element at maximum excursion in the distal direction of the introduction aid which has been fitted to the distal connection part in order to limit the movement thereof in the longitudinal direction, and at a kit comprising this connection element and this introduction aid. The limiting case of an outer tube which is perforated along the extent on the distal connector of the connection element comprises one or more tongues.

It is likewise possible for the functions "tongue/undercut" on the one hand and "retaining means" on the other hand to be exchanged with one another, that is to say the connection element has tongue and undercut, whereas the introduction aid possesses the retaining means. The present invention thus also embraces a connection element for connecting an introduction aid which is used for stretching one end of a guide wire and securing the guide wire in a dispenser tube to the dispenser tube, which element has a proximal connector for fastening the distal end of the dispenser tube, an essentially tubular distal connector to be pushed onto the introduction aid, and a central piece which is located between them and has an advancing surface which is freely accessible from outside, there being present in the wall of the distal connection part a U-shaped slit extending in the longitudinal direction, so that a tongue which can be pressed into the inside is formed between the legs of the U-shaped slit open towards the proximal end, and the distal connection part having at the distal end an undercut, and an introduction aid for stretching one end of a guide wire and securing the guide wire in a dispenser tube, which aid can be connected by such a connection element to the dispenser tube and has an elongate hollow element open at both ends, with a cylindrical section which can be pushed into the distal connector of the connection element and remains displaceable therein in the longitudinal direction after connection has taken place, and a conical section which tapers towards the distal end, there being present on the cylindrical section of the introduction aid a retaining means which grips the undercut of the distal connection part at maximum excursion in the distal direction of the introduction aid which has been inserted into the distal connection part in order to limit the movement thereof in the longitudinal direction, and a kit comprising this introduction aid and this connection element.

Preferred embodiments of the invention are represented in the dependent claims.

For the sake of a better overall view and of clarity, the invention is described in detail hereinafter only with reference to the embodiment "introduction aid with tongue and undercut and connection element with retaining means". However, a person of average skill in the art is able without problems to apply the explanations to the converse embodiments "connection element with undercut and introduction aid with tongue and retaining means" and "connection element with tongue and undercut and introduction aid with retaining means".

The U-shaped slit in the introduction aid can extend both in the area of the cylindrical section and in the area of the conical section or over both sections. The end of the tongue which is fixed and merges into the wall is preferably situated at the transition from the cylindrical section to the conical section or in the cylindrical section. When the inwardly pressed tongue makes contact with the guide wire it secures the latter against unwanted displacement in the longitudinal direction. In order to improve the securing effect, the tongue can have a kink so that the free end of the tongue is bent off into the inside of the hollow element. The tongue may be thicker than, thinner than or identical to the wall thickness of the cylindrical section.

The undercut at the proximal end of the essentially cylindrical section is preferably annular and may, for example, be an outwardly pointing annular beading or an annular groove which is located on the outer surface of the cylindrical section.

Configurations which facilitate grip by the user's hand, for example in the form of gripping plates or gripping grooves, can be attached on the outer surface of the essentially cylindrical section of the introduction aid.

The internal diameter of the cylindrical section of the introduction aid is suited to the external diameter of the tubular distal connector of the connection element so that the latter can be pushed into the cylindrical section. A clamping fit on the connector is achieved by pushing the introduction aid in the proximal direction onto the connector until the tongue is pressed into the inside of the connector and, by means of the spring action, fixes the connector in the cylindrical section of the introduction aid. The inwardly pressed tongue secures the guide wire against displacement in the longitudinal direction. An additional kink in the tongue acts as a sort of notch for the clamping fit of the introduction aid according to the invention on the distal connector of the connection element according to the invention.

The retaining means on the connection element prevents, due to its grip on the undercut of the introduction aid, the latter being completely detached from the connector when it is moved in the distal direction to detach the guide wire. The retaining means is preferably located on the distal end of the connection element so that the tongue of the introduction aid is released on maximum excursion of the introduction aid in the distal direction and thereby the guide wire running in the inside of the introduction aid can be displaced and, during this, the cylindrical section of the introduction aid is still guided by the tubular distal connector. For example, the retaining means can have the form of at least one springy shackle which is arranged in the longitudinal direction and is open towards the distal end and which has on its distal end an inwardly directed lug and runs along part of the outer surface of the tubular distal connector. Two springy shackles are preferred. The lug on the shackle grips the undercut on the proximal end of the cylindrical section of the introduction aid when the introduction aid is connected and the excursion of the introduction aid in the distal direction is maximal, and thus prevents the introduction aid being able to move further in the distal direction and becoming completely detached from the connection element. In the case of an undercut in the form of an annular beading, for example, the lug contacts the annular beading, and in the case of an annular groove the lug engages in this groove. The springiness of the shackle(s) can be overcome on application of appropriately more force in the distal direction, that is to say the beading forces the shackle(s) apart, or the lugs of the shackles slip out of the annular groove, and the introduction aid can thus also be detached completely from the connection element if required. The springiness of the shackle(s) can likewise be overcome when the introduction aid and the connection element are assembled for the first time or once again.

As already mentioned, the internal diameter of the introduction aid is suited to the external diameter of the tubular distal connector of the connection element. It is advantageous to choose the external diameter of the connector to correspond to the external diameter of the dispenser tube, because it is then possible for the introduction aid according to the invention with transport securing function also in some circumstances to be fitted directly onto the dispenser tube without using the connection element.

The central piece of the connection element connects the distal and the proximal connector and has an is advancing surface which is accessible from the outside. The central piece can be, for example, simply an elongate plate, one side of which represents the advancing surface. In a preferred embodiment, the plate has gripping grooves on its side facing away from the advancing surface.

The proximal connector is used to fasten the connection element to the dispenser tube, in particular in such a way that the guide wire can emerge from the dispenser and, running through the central piece, can be introduced into the distal connector and the introduction aid in which it can then be clamped firmly by the tongue. In the simplest case, the proximal connector can be, for example, a narrow clip which is connected to the central piece and is clamped onto the wall of the dispenser tube at one point in the extent of the tube. However, preferred embodiments of the connection element are those in which the proximal connector has the form of a sleeve which is closed at the distal end apart from an opening for the guide wire to pass through and into which the distal end of the dispenser tube is pushed and clamped firmly therein, or has the form of a tube with two different internal diameters, with the larger internal diameter pointing towards the proximal end and being suitable for the reception and clamping fastening of the distal end of the dispenser tube.

The introduction aid according to the invention and the connection element according to the invention may consist of the same or different materials, it also being possible to use different materials within one part. Both the introduction aid and the connection element are preferably in each case made of plastic in one piece, advantageously by the injection moulding method for reasons of cost. Suitable examples are conventional thermoplastic polymers or thermoplastic elastomers. Polyolefins are particularly suitable, for example polypropylene, both low and high density polyethylene, or alternatively use may also be made of acrylic/butadiene/styrene terpolymers, impact-resistant polystyrene or polyoxymethylene. The polymeric material has an elasticity such that although the tongue of the introduction aid is movable, that is to say is flexible at its point of connection to the hollow element, it possesses at the same time a sufficient restoring force in order to return to its starting position or to near its starting position when the introduction aid is advanced in the distal direction on the distal connector of the connection element. Similar statements also apply to the retaining means in the form of springy shackles. In this case, the springiness of the shackles must be sufficiently great, through selection of the material and/or shape of the shackles, that the undercut on the proximal end of the cylindrical section of the introduction aid cannot be overcome too easily on longitudinal displacement, for example that the beading cannot force the shackles apart too easily.

The introduction aid according to the invention and the connection element according to the invention can be used for transporting guide wires, preferably Seldinger wires with a J-shaped tip, in conventional dispenser tubes, the wire being secured against unwanted slipping out, it being possible to release the transport securing with one hand and to advance the guide wire likewise with one hand in order to introduce it into the catheter set. The introduction aid and connection element can be used with conventional dispenser tubes without the latter needing to be subjected to any changes therefor. The dispenser tube is normally converted into a coil and kept in shape with the aid of separate clips which have longitudinal slits and are designed as double or triple clasps. The connection element is connected with its proximal connector to the distal end of the dispenser tube. The introduction aid is connected to the distal connector of the connection piece by pushing it onto the tubular connector. For transport, the guide wire runs from the dispenser tube through or over the proximal connector of the connection element, over the advancing surface of the central piece, through the tubular distal connector and through the introduction aid at whose pointed distal end the J-shaped tip of the wire emerges. During transport, the introduction aid is pushed as far as possible in the proximal direction onto the connection element so that the tongue of the introduction aid is pressed inwards as described previously and fixes the wire. If the guide wire is now to be introduced into a catheter kit, it is necessary to release the transport securing and push the wire out of the dispenser. For this purpose, the user holds the connection element with fitted introduction aid in one hand and pushes the introduction aid in the distal direction until the retaining means engages, after which the tongue is released and the guide wire becomes displaceable. By gripping the advancing surface, preferably with the thumb, the user is now able to push the wire back first to stretch the curved tip, introduce the introduction aid into the attachment of the catheter kit and then advance the wire.

BRIEF DESCRIPTION OF THE DRAWINGS

The invention is now to be explained in detail by means of two embodiments of the introduction aid and two embodiments of the connection element in the following figures.

FIG. 1 is a top view of a connection element with a retaining means in the form of two shackles (proximal and distal connector in cross-section).

FIG. 2 is a top view of an introduction aid with tongue and annular beading.

FIG. 2A is a top view of an introduction aid with tongue and annular groove.

FIG. 3 is a side view of the connection element from FIG. 1 (proximal connector in cross-section).

FIG. 4 is a side view of the introduction aid from FIG. 2.

FIG. 6 is a depiction of a section corresponding to FIG. 5 but with inserted guide wire.

FIG. 7 is a depiction of a section similar to FIG. 6 with the difference that the introduction aid is pushed further in the proximal direction onto the distal connector of the connection element.

FIG. 8 shows a dispenser tube which is converted into a coil and to which the connection piece is connected and the introduction aid is fitted.

DETAILED DESCRIPTION OF THE INVENTION

Figure 5:
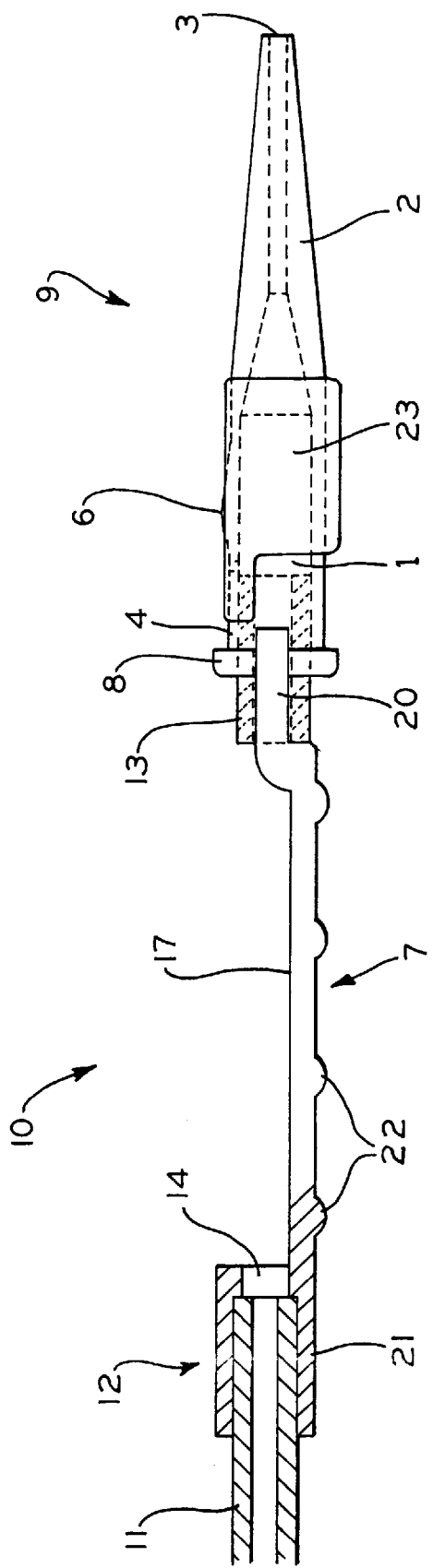
FIG. 5 is a side view of the connection element from FIG. 1 which is connected to a dispenser tube and is fitted with the introduction aid from FIG. 2, with the introduction aid being in maximum excursion in the distal direction on the distal connector (distal and proximal connector in cross-section).

FIGS. 1 and 3 show a connection element 10 with proximal connector 12, central piece 7 and distal connector 13. The proximal connector 12 has the form of a cylindrical sleeve 21 which is open towards the proximal end and possesses on its distal end an opening 14 for the guide wire 15 to pass through. On the underside, the sleeve 21 is connected at its distal end to the central piece 7 which has the form of an elongate plate. The upper side of the central piece 7 represents the so-called advancing surface 17, and on the underside there are four elongate gripping ridges 22 which run transverse to the longitudinal direction. The tubular distal connector 13 is connected to the proximal end of the central piece 7. It is, just like the proximal connector 12, connected via its lower section to the central piece 7. Likewise connected to the proximal end of the central piece 7 are two springy shackles 20 which are a bit swung upwards, starting from the central piece 7, in order then to run parallel to the longitudinal axis of the tubular distal connector 13 at its widest point along the outer surface thereof. On the distal end of the shackles 20 there is in each case a lug 19 which is directed inwards, that is to say towards the distal connector 13. The distance of the shackles 20 (without lug 19) from the outer surface of the distal connector 13 is only slightly more than the total of the thickness of the wall 4 of the cylindrical section 1 of the introduction aid 9 and the thickness of the annular beading 8. The distal connector 13 projects in the distal direction beyond the shackles 20 in order to provide sufficient hold for a fitted introduction aid 9 even when the latter is in its maximum excursion in the distal direction.

FIGS. 2 and 4 show an introduction aid 9 according to the invention comprising a cylindrical section 1 and a conical section 2 which tapers towards the distal end 3. In the cylindrical section 1 there is a U-shaped slit 5 so that a tongue 6 is formed in the wall of the cylindrical section 1. The tongue 6 is kinked on the upper side to improve locking of the distal connector 13 when the introduction aid 9 is pushed onto one of the latter. At its proximal end, the cylindrical section 1 possesses an annular beading 8 for engagement in the shackles 20 of the connection element. In addition, the cylindrical section 1 is encircled by gripping plates 23 which facilitate gripping by the user. The interior design of the introduction aid 9 is also evident in FIG. 4. It is clear that the inner walls of the introduction aid 9 taper even at the transition of the cylindrical section to the conical section 2 and then an inner bore with a constant cross-section leads to the distal end 3.

FIGS. 5 to 7 depict the connection element 10 and the introduction aid 9 in the assembled state. Since the elements evident herein are essentially the same as those already described, only the differences will be dealt with hereinafter. In all of FIGS. 5 to 7, the proximal connector 12 is fitted onto the distal end of a dispenser tube 11. The internal diameter of the connector 12 approximately corresponds to the external diameter of the dispenser tube 11 so that the latter, normally elastic, dispenser tube 11 can be pushed into the proximal connector 12 and is fastened in the latter by a clamping fit. It is likewise evident in all three figures that the external diameter of the distal connector 13 corresponds to the external diameter of the dispenser tube 11. The internal diameter of the cylindrical section 1 of the introduction aid is in this case only slightly larger than the external diameter of the distal connector 13 of the connection element 10 so that the cylindrical section 1 can be pushed onto the distal connector 13.

FIGS. 5 and 6 depict an introduction aid 9 which is pushed onto the distal connector 13 of the connection piece 10 with maximum excursion in the distal direction, that is to say it is advanced so far in the distal direction that the lugs 19, which are not visible in FIGS. 5 and 6, of the shackles 20 grip the beading 8 of the introduction aid 9 and prevent it possibly being moved further in the distal direction and becoming completely detached from the connection element 10, and complete detachment of the introduction aid 9 from the connection element 10 is possible only by forcing the shackles 20 apart by overcoming their springiness. It can be inferred from the figures that the introduction aid 9 is still, even in this position of maximum excursion in the distal direction, guided by a part of the distal connector 13 which is surrounded by the cylindrical section 1. In this position the distal connector 13 does not yet interact with the tongue 7, that is to say the tongue 7 is unaltered by comparison with the unconnected state of the introduction aid 9; it is located in the wall 4 of the cylindrical section 1 and is not pressed inwards. This in turn means that the guide wire 15 which is depicted in FIG. 6 and runs inside is freely displaceable in this position of the introduction aid 9, for example by the user displacing the wire 15 pressing from above against the advancing surface 17.

FIG. 7 now shows the introduction aid 9 pushed further in the proximal direction onto the connector 13. The free ends of the tongue 6, which can be pressed in, are preferably even in the starting position (FIG. 6) located somewhat inside the wall 4 of the cylindrical section 1 (not depicted in FIG. 6) so that when the introduction aid 9 is displaced on the connector 13 in the proximal direction the tongue 6 is pushed into the interior of the connector 13 as represented in FIG. 7. If the introduction aid 9 is pushed further in the proximal direction beyond the kink 6 in the tongue, the tongue 6 is pressed by the distal connector 13 further inwards against the catheter guide wire 15 and fixes the latter inside the introduction aid 9, and thus inside the entire dispenser tube 11, against displacement in the longitudinal direction.

FIG. 8 shows the connection element 10 with fitted introduction aid 9, which are connected to the distal end of a dispenser tube 11 which is converted into a coil and held in this shape by two double clips 18. The dispenser tube 11 is preferably left in the coiled arrangement especially also when the guide wire 15 stored therein is introduced into a catheter kit. The guide wire depicted in FIGS. 6 to 8 is a Seldinger wire with a tip which is curved in a J shape.

Figure 10:
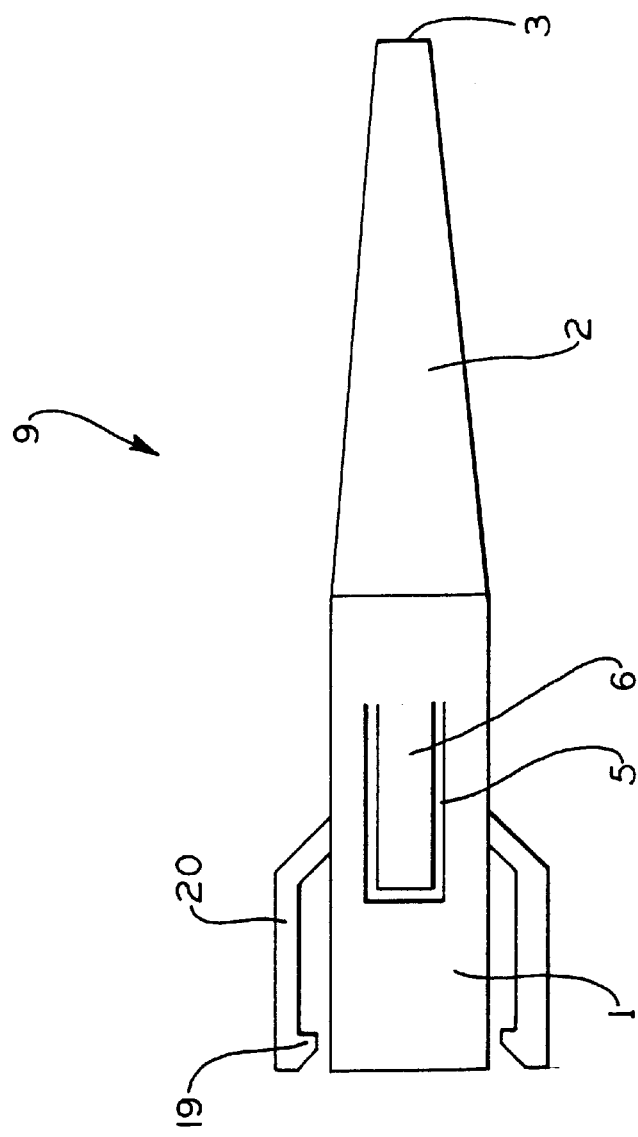
FIG. 10 is a top view of an introduction aid with tongue and a retaining means in the form of two shackles.
Figure 9:
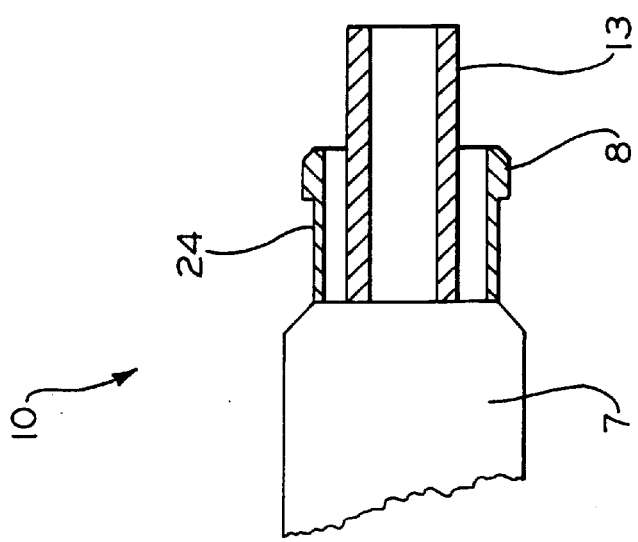
FIG. 9 is a depiction of a section of a distal connecting part of a connection element with outer tube.

FIGS. 9 and 10 show embodiments of the present invention with reversed functionality in respect of the undercut and the retaining means. FIG. 9 depicts the distal connector 13 of a connection element 10 which is surrounded by an outer tube 24. The outer tube 24 has at its distal end an annular beading 8. The tubular distal connector 13 is longer than the outer tube 24 and projects beyond the latter in the distal direction. The radial distance between the distal connector 13 and outer tube 24 corresponds at least to the thickness of the wall 4 of the cylindrical section 1 of the introduction aid 9 so that the latter can be pushed onto the distal connector 13. The distal connector 13 is connected in the proximal direction to the central piece 7 which is depicted only in part here, and then to the proximal connector 12 which is not depicted here and can be designed as in FIGS. 1, 3 and 5 to 7.

The introduction aid 1 depicted in FIG. 10 consists, like the introduction aid 1 illustrated in FIGS. 2 and 4, of a conical section 2 and a cylindrical section 1 which has a U-shaped slit 5 forming the tongue 6. Two springy shackles 20 which are open towards the proximal end are arranged opposingly on the outside of the cylindrical section 1 and have on each of their proximal ends a lug 19 which is directed inwards. The internal diameter of the cylindrical section 1 is slightly larger than the external diameter of the distal connector 13 so that it can be pushed onto the latter. The distance of the shackles 20 from the outside of the cylindrical section 1 is selected so that the shackles 20 are able to grip round the outer tube 24 of the connection element 10, and the lugs 19 are in contact with the annular beading 8 when the introduction aid 9 is fitted onto the distal connector 13 with maximum excursion, and prevent further movement in the distal direction.

What is claimed is:

1. An apparatus for stretching one end of a catheter guide wire and for securing the catheter guide wire in a dispenser tube, said apparatus comprising:

an elongate hollow element having an open distal end and an open proximal end, said elongate hollow element including a cylindrical section having an undercut and a conical section, said conical section tapering away from said cylindrical section, a U-shaped slit in a wall of said elongate hollow element and extending in the longitudinal direction of said elongate hollow element, said U-shaped slit defining a flexible tongue depressible into said elongate hollow element;

a connection element connected to said elongate hollow element, said connection element comprising a proximal connector adapted to connect to a dispenser tube, a tubular distal connector inserted into said cylindrical section such that said elongate hollow element and said connection element may move longitudinally relative to one another between first and second positions, a central section interconnecting said proximal connector and said tubular distal connector, said central section having an advancing surface; and a retainer disposed on one of said central section and said distal connector, said retainer to grip said undercut in said second position, whereby in said first position, said flexible tongue may be pressed into said tubular distal connector to engage a catheter guide wire, and in said second position, said flexible tongue may be released from engagement with a catheter guide wire.

2. The apparatus of claim 1, wherein said undercut comprises an annular bead.

3. The apparatus of claim 1, wherein said undercut comprises an annular groove.

4. The apparatus of claim 1, wherein said cylindrical section includes a gripping plate.

5. The apparatus of claim 1, wherein said retainer is disposed on one of said central section and said distal connector such that said tubular distal connector remains engaged with said cylindrical section in said second position.

6. The apparatus of claim 1, wherein said retainer comprises at least one resilient arm opening toward an end of said tubular distal connector, said resilient arm having an inwardly directed lug.

7. The apparatus of claim 1, wherein said proximal connector comprises an annular sleeve adapted to receive and hold a dispenser tube, said annular sleeve having an opening for a catheter guide wire to pass through.

8. The apparatus of claim 1, wherein said proximal connector comprises a tube, said tube having a first end adapted to receive a catheter guide wire and a second end adapted to receive and hold a dispenser tube.

9. An apparatus for stretching one end of a catheter guide wire and for securing the catheter guide wire in a dispenser tube, said apparatus comprising:

an elongate hollow element having an open distal end and an open proximal end, said elongate hollow element including a cylindrical section and a conical section, said conical section tapering away from said cylindrical section, a U-shaped slit in a wall of said elongate hollow element and extending in the longitudinal direction of said elongate hollow element, said U-shaped slit defining a flexible tongue depressible into said elongate hollow element;

a connection element connected to said elongate hollow element, said connection element comprising a proximal connector adapted to connect to a dispenser tube, a tubular distal connector inserted into said cylindrical section such that said elongate hollow element and said connection element may move longitudinally relative to one another between first and second positions, an outer tube disposed around said tubular distal connector adapted to receive said cylindrical section, said outer tube having an undercut, and a central section interconnecting said proximal connector and said tubular distal connector, said central section having an advancing surface; and a retainer disposed on said cylindrical section, said retainer to grip said undercut in said second position, whereby said flexible tongue may be pressed into said tubular distal connector to engage a catheter guide wire in said first position, and said flexible tongue may be released from engagement with a catheter guide wire in said second position.

10. The apparatus of claim 9, wherein said tubular distal connector projects beyond said outer tube.

* * * * *